United States Patent
Patane

(10) Patent No.: US 6,982,158 B2
(45) Date of Patent: Jan. 3, 2006

(54) EXTRACTION AND PURIFICATION OF PHOSPHODIESTERASE 1

(75) Inventor: Michael Patane, Seaforth (AU)

(73) Assignee: Protech Research Pty Ltd, Seaforth (AU)

( * ) Notice: Subject to any disclaimer, the term of this patent is extended or adjusted under 35 U.S.C. 154(b) by 0 days.

(21) Appl. No.: 10/733,857

(22) Filed: Dec. 11, 2003

(65) Prior Publication Data

US 2004/0229332 A1 Nov. 18, 2004

(30) Foreign Application Priority Data

May 14, 2003 (AU) .............................. 2003902303

(51) Int. Cl.
*C12N 9/22* (2006.01)
(52) U.S. Cl. ...................... 435/199; 435/195; 435/196; 435/183; 435/814; 800/320
(58) Field of Classification Search ................ 435/199, 435/196, 195, 183, 814; 800/320
See application file for complete search history.

(56) References Cited

U.S. PATENT DOCUMENTS 3,516,907 A * 6/1970 Holle et al. .................... 435/89
5,879,916 A * 3/1999 De-Eknamkul et al. ..... 435/155

OTHER PUBLICATIONS

Harvey et al, 1967, Biochemistry, vol. 6, No. 12, pp. 3689-3694.*
Hsin et al, 1998, Blood, vol. 92, No. 9, pp 3268-3276.*
IUBMB Enzyme Nomenclature, "EC 3.1.4.1" accessed Aug. 12, 2004 www.chem.qmul.ac.uk.iumbm/enzyme/EC3/1/4/1.html.*
Chae, H.J., et al., "Utilization of Brewer's Yeast Cells for the Production of Food-Grade Yeast Extract. Part 1: Effects of different enzymatic treatments on solid and protein recovery and flavour characteristics", Bioresource Technology 76(3): 253-258, 2000.
Kozma, P., et al., "Purification and Properties of a Phosphodiesterase and Nucleotide Pyrophosphatase From Root Callus Tissues of Vine Shoots", Acta Agronomica Academiae Scientiarum Hungaricae 28(3-4):281-294, 1979.
La Marra-Phillips, A., "A Study of Phosphodiesterase in the fission yeast Schizosaccharomyces Pombe", UMI, Order No. DA9818617, From: Diss Abstr. Int., B 58(12):6377, 1998.
Nakabayashi, T., et al., "Phosphodiesterase I in Cultured Cells of *Mentha Arvensis*", Phytochemistry 39(5):1013-1016, 1995.
Sander, M., et al., "Partial Purification of Pdel from *Saccharomyces cerevisiae*: Enzymatic Redundancy for the Repair of 3'-Terminal DNA Lesions and Abasic Sites of Yeast", Biochemistry 36(20):6100-6106, 1997.
Ueda, N., et al., "Marked Activation of the *N*-acylphosphatidylethanolamine-hydrolyzing phosphodiesterase by divalent cations", Biochimica et Biophysica Acta 1532(1-2):121-127, 2001.
Vogel, A., et al., *ElaC* Encodes a Novel Binuclear Zinc Phosphodiesterase, Journal of Biological Chemistry 277 (32), 29078-29085, 2002.
Washburn, K.B., et al., "Comparison of Mechanical Agitation and Calcium Shock Methods for Preparation of a Membrane Fraction Enriched in Olfatory Cilia", Chemical Senses 27(7):635-642, Sep. 2002.
Wold, W.S.M., et al., "Demonstration in *Aspergillus niger* of adenyl cyclase, a cyclic adenosine 3', 5'-monophosphate-binding protein, and studies on intracellular and extracellular phosphodiesterases" Canadian Journal of Microbiology, 20(11):1567-1576, 1974.
Yu, J., et al., "Identification and Characterisation of a Human Calmodulin-Stimulated Phosphodiesterase PDE1B1", Cellular Signalling 9(7):519-529, Nov. 1997.

* cited by examiner

*Primary Examiner*—Leon B. Lankford, Jr.
*Assistant Examiner*—Allison M. Ford
(74) *Attorney, Agent, or Firm*—Christensen O'Connor Johnson Kindness PLLC

(57) ABSTRACT

A process for purifying a phosphodiesterase 1 (PDE-1) from a cell including heating an extract of a cell formed from a solution including at least one divalent cation, to increase the specific activity of PDE-1 in the extract.

12 Claims, No Drawings

EXTRACTION AND PURIFICATION OF PHOSPHODIESTERASE 1

FIELD OF THE INVENTION

The invention relates to extracting and purifying an enzyme from a cell, particularly, but not exclusively, to extracting and purifying a 5' phosphodiesterase from a barley cell.

BACKGROUND OF THE INVENTION

Phosphodiesterase 1 (orthophosphoric diester phosphohydrolase, EC 3.1.4.1; herein "PDE-1") is an enzyme that catalyses the hydrolysis of a phosphodiester bond at the 3' hydroxyl end of ribopolynucleotide to yield a 5' ribonucleotide.

PDE-1 is particularly important to food and pharmaceutical industries because the 5' ribonucleotides produced by PDE-1—mediated cleavage of yeast RNA are useful as flavour enhancers.

Barley cells or rootlets are used in the food industry as a source of PDE-1.

The processes for purification of PDE-1 from barley rootlets tend to be difficult to operate on a commercial scale, in terms of requiring sophisticated extraction and separation techniques, multiple steps and expensive reagents and equipment. Some processes are characterised by an unacceptable loss or wastage of PDE-1. Other processes tend to produce a final product that has a sub-optimal specific activity.

In view of the above, there is a need for improved processes for purification of PDE-1.

SUMMARY OF THE INVENTION

The invention seeks to at least minimise one or more of the above identified problems or limitations and/or to provide an improved process for purification of PDE-1.

In one aspect, the invention provides a process for purifying PDE-1 from a cell. The process includes the step of heating an extract of a cell formed from a solution including at least one divalent cation, to increase the specific activity of PDE-1 in the extract.

In another aspect, the invention provides a process for purifying PDE-1 from a barley cell. The process includes the following steps:
(a) releasing PDE-1 from the cell into a solution including calcium and magnesium to form an extract; and
(b) heating the extract to increase the specific activity of PDE-1 in the extract.

In another aspect, the invention provides a process for purifying PDE-1 from a barley cell. The process includes the following steps:
(a) releasing PDE-1 from the cell into a solution including calcium and magnesium to form an extract;
(b) heating the extract to increase the specific activity of PDE-1 in the extract; and
(c) utilising anion exchange chromatography to purify PDE-1 from the heated extract.

Typically the cell is a barley cell, such as a cell derived from a barley rootlet.

In another aspect, the invention provides PDE-1 produced by the process of the invention.

In another aspect, the invention provides a cell including PDE-1 produced by the process of the invention.

In another aspect, the invention provides a process for producing a ribonucleotide. The process includes the step of contacting a polyribonucleotide with PDE-1 produced by the process of the invention, to produce the 5' ribonucleotide.

In another aspect, the invention provides a ribonucleotide produced by the above described process.

DETAILED DESCRIPTION OF THE EMBODIMENTS

As described herein, the inventor has found that heat treatment of an extract of a barley cell or rootlet in a solution comprising at least one divalent cation permits the specific activity of the extract to be increased. For example, the specific activity of a heat treated extract of a barley rootlet formed from a solution comprising calcium and magnesium was observed to increase 2.6 fold over a non heat treated sample ($312.6 \times 10^{-3}$ compared with $122 \times 10^{-3}$ μmoles/min/mL). Further, a heat treated extract containing calcium and magnesium was observed to have an improved specific activity ($78 \times 10^{-3}$ μmoles/min/mL) compared with a heat treated extract containing no calcium and magnesium ($46 \times 10^{-3}$ μmoles/min/mL).

This is a significant finding because it permits heat treatment, a purification step that is relatively simple to operate on a commercial scale, to be implemented with minimal loss of activity of PDE-1.

It is believed that the specific activity of the extract is increased because the divalent cation protects PDE-1 from denaturation at temperatures at which other proteins in the extract, including phosphomonoesterase, are degraded.

Typically, the at least one divalent cation in the solution may be magnesium and/or calcium. For example, the solution may contain $MgCl_2$ and/or $CaCl_2$.

The magnesium and calcium ions may be included in the extract in an amount to permit control of the denaturation of PDE-1 when the extract is heated. Typically, magnesium and calcium are included in the extract in an amount to at least limit the denaturation of PDE-1 when the extract is heated. For example, the concentration of calcium may be less than 100 mM and the concentration of magnesium may be less than 100 mM.

A concentration of calcium and magnesium in a range between about 10 to 50 mM is particularly useful as further down stream processing of the extract for further purification, such as anion exchange chromatography, may require removal of calcium and magnesium. Accordingly a concentration of calcium ions of about 50 mM and a concentration of magnesium ions of about 50 mM is particularly useful.

It is believed that phosphomonoesterase is a major constituent of an extract of a barley rootlet. Thus, the extract is typically heated to a temperature that permits denaturation of phosphomonoesterase, or otherwise, destruction of phosphomonoesterase activity in the extract. As described herein, temperatures less than 80° C. are suitable for this purpose.

It is particularly advantageous to heat the extract to between about 45 and 75° C. because at temperatures approaching 70° C. and above, PDE-1 activity may be lost. Accordingly, a temperature of about 60° C. is particularly useful.

The inventor has also found that the purification of PDE-1 from a barley cell extract can be improved by extracting a barley cell homogenate at 4° C. in a solution including magnesium and calcium. Specifically, as described herein, the specific activity of an extract comprising calcium and magnesium after maintenance at 4° C. was found to be $92 \times 10^3$ μmoles/min/mL as compared with the activity of an extract maintained at 4° C. in the absence of calcium and magnesium ($75 \times 10^3$ μmoles/min/mL).

It is believed that maintenance of such an extract at 4° C. is important because it permits PDE-1 to disassociate from solids in the extract, and accordingly, to solubilise into the liquid phase of the extract, prior to further processing of the extract, such as a heat treatment step or a chromatographic separation step. The calcium and magnesium are believed to be important for limiting hydrolysis of the enzyme during the maintenance of the extract at 4° C.

Thus in accordance with the invention, a process for purifying PDE-1 from a barley cell includes the following steps:
(a) releasing PDE-1 from the cell into a solution including calcium and magnesium to form an extract; and
(b) heating the extract to increase the specific activity of PDE-1 in the extract.

Typically, the extract is maintained in conditions for promoting solubilisation of the phosphodiesterase in the extract prior to heating the extract.

The extract may be maintained at less than 10° C. for less than 5 days. For example, the extract may be maintained between 0 to about 4° C. for between about 1 to 48 hours.

It is particularly advantageous to maintain the extract for 24 hours at 4° C. as this improves the speed of purification protocols that comprise further purification steps.

The inventor has further found PDE-1 can be purified to virtual homogeneity from a barley cell extract by a process including the following steps:
(a) releasing PDE-1 from the cell into a solution including calcium and magnesium to form an extract;
(b) heating the extract to increase the specific activity of PDE-1 in the extract; and
(c) utilising chromatography to purify PDE-1 from the heated extract.

As described herein, PDE-1 can be further purified from a heat treated barley cell extract by anion exchange chromatography. Accordingly, typically, in step (c), anion exchange chromatography is utilised to purify PDE-1 from the heated extract.

The inventor has found that calcium and magnesium ions tend to limit binding of PDE-1 during anion exchange chromatography. Accordingly, typically the extract is desalted before anion exchange chromatography. One way of desalting to remove magnesium and calcium ions is by ultrafiltration. Alternatively, a preparative de-salting column, such as a Hi trap 26/10 desalting column can be used. It is particularly advantageous to remove substantially all of the calcium and magnesium from the extract prior to anion exchange chromatography for the purpose of maximising the yield of PDE-1 purified from the anion exchange column.

Typically, the extract is maintained in conditions for promoting solubilisation of the phosphodiesterase in the extract prior to heating the extract.

In the processes of the invention described above, the extract of the barley cell is typically produced by homogenising barley rootlets in an appropriate buffer. One way of homogenizing rootlets is by use of a blender, such as a Waring blender. Alternatively, the extract may be produced by milling barley rootlets in an appropriate buffer.

The solution into which the PDE-1 from the cell is released to form an extract is typically a buffer for controlling pH. Solutions prepared from Trisma base are examples of such a solution. A solution having a concentration of no more than about 100 mM Tris is suitable, however a solution having a concentration between about 20 to 50 mM Tris, for example, 25 mM Tris is particularly advantageous because as described herein, this concentration of Tris is compatible with, and permits separation of PDE-1 on, an anion exchange column.

It will be understood that the processes of the invention are useful for purifying PDE-1 from cells other than barley cells. Further, it will be understood that processes of the invention are useful for isolating barley PDE-1 from cells that contain a recombinant nucleic acid molecule that encodes barley PDE-1. Examples of such cells include bacterial cells and yeast cells.

In another aspect, the invention provides a process for producing a ribonucleotide. The process includes the step of contacting a polyribonucleotide with PDE-1 produced by the process of the invention, to produce the ribonucleotide. Preferably the polyribonucleotide is derived from yeast RNA, such as yeast ribosomal RNA.

EXAMPLE 1

Materials and Equipment

Germinating barley seeds (Schooner variety) were obtained from Barrett Burston Malting, (Thornleigh, NSW, Australia). Thymidine 5' monophosphate p-nitrophenyl ester, Trisma base, $MgCl_2$, $CaCl_2$, p-nitrophenyl-phosphate, Baker's yeast RNA, bovine serum albumin, guanosine 5'-monophosphate, potassium dihydrogen orthophosphate were all supplied by Sigma Aldrich (Castle Hill, NSW Australia).

Yeast rRNA was prepared as a 3 mg/mL standard solution in RNAse free Milli Q water (pH7.0) in a clean room environment and immediately frozen to minus 80° C. and stored until required.

Guanosine 5'-monophosphate was prepared as a 1% (w/v) stock by dissolving in Milli Q water and storing at −20° C. Working solutions were prepared by diluting the stock solution to 0.01% (w/v).

The buffer used for FPLC was 25 mM Tris HCl (pH 8.9). The eluent buffer included 1 M NaCl.

For the HPLC analysis, solvent (A) was 0.02M potassium dihydrogen orthophosphate (pH 6.5) solution while solvent (B) was a 40% methanol (HPLC grade) and 60% Milli Q water mixture (pH 6.5).

All solvents and buffers were degassed and filtered prior to use by passing each solution through a Millipore membrane filter, pore size 0.45 μm under vacuum for 5 minutes.

An Amersham Pharmacia AKAT gradient processing FPLC system complete with a 900 model monitor, lamp and detector (set at 280 nm), 920 model pump and Frac 950 fraction collector interfaced to a Compaq Deskpro Pentium III computer supporting Unicorn analytical software was used for all protein purification. The columns used included a Hi Trap 26/10 desalting column connected to a Super loop 50 (to facilitate larger injection volumes), a 16/10 Hi-Load Q anion exchange column with a final purification undertaken on a Mono Q HR 5/5 column.

The HPLC system used for the analysis of 5' nucleotides was a Shimadzu Liquid Chromatography unit, consisting of a Shimadzu pump (model LC-10Ai) with an on-line degassing unit, SCL-10A system controller, SPD-M10A diode array detector and a column oven (set at 30° C.), the system was controlled by a Dell Pentium III computer operating a Shimadzu class VP (version 5.03) analytical software program. The column used for the analysis of 5' ribonucleotides was an Activon Goldpak HPLC column (250 mm×4.6 mm, 5 mm particle size and 10 nm pore size). Peak heights were determined from chromatograms recorded at both 245 nm and 280 nm.

A Pharmacia LKB UV-Visible spectrophotometer was also used to measure enzyme activity and was set at 410 nm with an aligned temperature control cell all controlled by a HP Pentium II computer operating a Biochrome 4060 enzyme kinetics software program.

EXAMPLE 2

Preparation of a Standard Curve for p-nitrophenol to Determine PDE-1 Activity

A solution of 10 mg/100 mL of p-nitrophenol was prepared in 50 mM Tris HCl (pH 8.9) to yield a concentration of 0.719 $\mu$moles/ml of p-nitrophenol. Dilutions were prepared in 50 mM Tris HCl (pH8.9) and read as a 4.1 mL sample size at 410 nm to directly correlate with the enzyme activity absorbances at each purification step.

EXAMPLE 3

Preparation of a Standard Curve for Protein to Determine PDE-1 Specific Activity Protein was determined using the BioRad micro assay procedure derived from the original method of Bradford utilising a standard curve produced for bovine serum albumin. Each analysis was conducted in duplicate requiring incubation at room temperature for 10 minutes with the absorbance measured at 595 nm. Standards were prepared in the range of 0.2 to 1.4 mg/mL of protein.

EXAMPLE 4

Enzyme Kinetics Assay

The assay solution consisted of 0.1 mL of purified PDE-1, 2.0 mL of 50 mM Tris HCl (pH 8.9), 1 mL of 1 mM thymidine 5' monophosphate p-nitrophenyl ester in 50 mM Tris HCl (pH 8.9) and 1 mL of a 50 mM $MgCl_2$ in 50 mM Tris HCl (pH 8.9). The reaction mixture was incubated at 37° C. for 30 minutes with the optical density of enzymatically produced p-nitrophenol measured at 410 nm each minute to determine the PDE-1 reaction kinetics.

The activity was determined by extrapolation against a standard curve with 1 unit of activity defined as the micromoles of p-nitrophenol produced from p-nitrophenyl ester per minute per mL of purified PDE-1. Specific activity was defined as the activity per milligram of purified PDE-1.

EXAMPLE 5

Confirmation of PDE-1 Activity

Confirmation of enzyme activity was undertaken by reaction of the purified enzyme with 3 mg/mL Baker's yeast RNA and measuring the 5'ribonucleotide products by reverse phase HPLC.

The HPLC column was equilibrated with 100% buffer A for 30 minutes at a flow rate of 1 ml.min ensuring the pressure remained below 180 Kpa. The ratio of solvent B in the elution system was increased linearly over 18 minutes to 40% then increased to 100% over the next 2 minutes and held for a further 2 minutes to flush any remaining strongly bound compounds. The system was automatically returned to its starting conditions over the following 8 minutes and stabilised on buffer A for a further 30 minutes before the next injection. The total analysis time was 60 minutes with elution performed at 30° C. oven temperature.

EXAMPLE 6

Preparation of Crude PDE-1 Extract 10 g of fresh barley rootlets were obtained from seeds that had been germinating for 5 days including a 2 day steep in 5 mg/kg gibberellic acid to facilitate enzyme extraction. The rootlets were dispersed in 100 mL 25 mM Tris-HCl (pH7.5) containing 50 mM $MgCl_2$ and 50 mM $CaCl_2$. This mixture was homogenised in a Waring blender at high speed for 1 minute and maintained at 4° C. for 24 hours to facilitate solubilisation of PDE-1.

The insoluble material was removed from the extract by filtering through double cheese cloth. The filtrate was then centrifuged at 15,000 rpm for 30 minutes at 4° C. to remove solids and the supernatant was passed through a 0.45 $\mu$M filter and stored at 4° C. in a sterile container with 0.01% sodium azide. This process formed the crude PDE-1 extract.

The activity and specific activity of the crude PDE-1 extract was then determined according to Examples 2 to 4 above.

EXAMPLE 7

Purification of PDE-1 from the Crude PDE-1 Extract

The first stage of the purification process involved the removal of heat labile enzymes (primarily Acid Phosphatase [Phosphomonoesterase (PME)] EC 3.1.3.2) and inhibitory proteins from the crude PDE-1 extract with the aim of reducing any loss of activity or damage to the structure of PDE-1. To inactivate PME, the crude extract was heated in a water bath to 60° C. and maintained at that temperature for 1 hour. The extract was then cooled to room temperature and the pH adjusted to 8.9. The extract was then filtered through a 0.45 $\mu$m filter.

The activity and specific activity of the heat treated PDE-1 extract was then determined according to Examples 2 to 4 above.

Ion exchange chromatography was then undertaken. A 100 mL sample of the extract was injected into a Super loop 50 column and desalted by FPLC on a Hi trap 26/10 desalting column at a flow rate of 7.0 mL per minute, to remove magnesium and calcium. The desalted fractions were then pooled and reloaded onto the Super loop column and passed through a Hi load 16/10 anion exchange column at 3.0 mL per minute to initially fractionate PDE-1. The isolated fraction was again desalted to remove the 1M NaCl elution buffer and was then purified by passing the fraction through the Mono Q HR 5/5 column at 1.5 mL per minute. A single peak was obtained and analysed for activity and specific activity according to Examples 2 to 4 above.

EXAMPLE 8

Purification Profile for PDE-1

The results for the purification of PDE-1 are shown in Table 1.

TABLE 1

| Sample | Activity | Specific activity | Purification factor |
|---|---|---|---|
| Crude extract | 169 | 122 | 1 |
| Heat treatment | 156.3 | 312.6 | 2.6 |
| Anion exchange | 267.5 | 1407.9 | 11.5 |

Activity: × $10^{-3}$ μmoles/min/mL
Specific activity: × $10^{-3}$ μmoles/min/mL/mg

EXAMPLE 9

Effect of Calcium and Magnesium on PDE-1 Activity of Crude Extract During Solubilisation at 4° C.

We sought to determine whether calcium and magnesium would have an effect on stabilisation of PDE-1 in the crude extract, or otherwise, on preserving or enhancing PDE-1 activity of the crude extract, during the step of solubilising PDE-1 at 4° C. that follows the homogenisation step described in Example 6.

To this end we maintained the homogenised extract at 4° C. in 25 mM Tris HCl (pH8.9): (i) in the absence of calcium and magnesium; (ii) with 5 mM $MgCl_2$ and 5 mM $CaCl_2$; and (iii) with 50 mM $MgCl_2$ and 50 mM $CaCl_2$.

We found that calcium and magnesium enhanced and indeed stabilised PDE-1. At 50 mM $MgCl_2$ and 50 mM $CaCl_2$, the PDE-1 activity was 22% greater than in the sample with no magnesium or calcium ($92 \times 10^3$ μmoles/min/mL compared to $75 \times 10^3$ μmoles/min/mL).

EXAMPLE 10

Effect of Calcium and Magnesium on PDE-1 Activity of Crude Extract During Heat Treatment We sought to determine whether calcium and magnesium would have an effect on stabilization of PDE-1 in the crude extract or otherwise on preserving or enhancing PDE-1 activity of the crude extract, during the step of heating PDE-1 as described in Example 7.

To this end, we incubated the crude extract at 60° C. for 1 hour in 25 mM Tris HCl (pH8.9): (i) in the absence of calcium and magnesium; (ii) with 5 mM $MgCl_2$ and 5 mM $CaCl_2$; and (iii) with 50 mM $MgCl_2$ and 50 mM $CaCl_2$.

We found that after heating, the activity dropped significantly in samples without magnesium and calcium and in samples with 5 mM $MgCl_2$ and 5 mM $CaCl_2$ by over 40% compared with samples with 50 mM $MgCl_2$ and 50 mM $CaCl_2$ ($46 \times 10^3$ μmoles/min/mL and $48 \times 10^3$ μmoles/min/mL compared with $78 \times 10^3$ μmoles/min/mL).

What is claimed is:

1. A process for purifying a phosphodiesterase 1 (PDE-1) from a cell including heating an extract of a cell formed from a solution including at least one divalent cation, to increase the specific activity of PDE-1 in the extract, wherein the concentration of the divalent cation is about 50 mM.

2. A process according to claim 1 wherein the divalent cation is magnesium or calcium.

3. A process according to claim 1 wherein the extract is heated to a temperature that permits depletion of phosphomonoesterase activity from the extract.

4. A process according to claim 3 wherein the extract is heated to less than 80° C.

5. A process according to claim 4 wherein the extract is heated to between about 45 and 75° C.

6. A process according to claim 5 wherein the extract is heated to about 60° C.

7. A process for purifying PDE-1 from a barley cell including:
    releasing PDE-1 from the cell into a solution including about 50 mM calcium and about 50 mM magnesium to form an extract; and
    heating the extract to between about 45 to 70° C. to increase the specific activity of PDE-1 in the extract.

8. A process according to claim 7 wherein the extract is maintained in conditions for promoting solubilization of the phosphodiesterase in the extract prior to heating the extract.

9. A process according to claim 8 wherein the extract is maintained at less than 10° C.

10. A process according to claim 9 wherein the extract is maintained at between 0 to about 4° C.

11. A process according to claim 7 comprising the further step of:
    utilizing chromatography to purify PDE-1 from the heated extract.

12. A process according to claim 11 wherein anion exchange chromatography is utilized to purify PDE-1 from the heated extract.

* * * * *